United States Patent [19]

Blumenthal

[11] Patent Number: 5,207,708
[45] Date of Patent: May 4, 1993

[54] ARTIFICIAL EYE LENS AND METHOD OF IMPLANTING SAME

[76] Inventor: Michael Blumenthal, 2 Egoz Street, Ramat Efal 52960, Israel

[21] Appl. No.: 779,050
[22] Filed: Oct. 18, 1991
[51] Int. Cl.⁵ .............................................. A61F 2/16
[52] U.S. Cl. ............................................................ 623/6
[58] Field of Search .................................................. 623/6

[56] References Cited

U.S. PATENT DOCUMENTS

| | | | |
|---|---|---|---|
| 4,504,981 | 3/1985 | Walman | 623/6 |
| 4,615,701 | 10/1986 | Woods | 623/6 |
| 4,990,159 | 2/1991 | Kraff | 623/6 |

Primary Examiner—Ronald Frinks
Attorney, Agent, or Firm—Sherman and Shalloway

[57] ABSTRACT

An intraocular lens comprising a central convex optical portion and two fixation loop appendages extending from the periphery of said optical portion and substantially in the horizontal plane thereof, characterized in that one of said loop appendages is double spring-like and curves from said periphery of said optical portion in a curvilinear "reverse S" shape, and the other said loop appendage extends from the same side of the periphery curving in the opposite direction in a curve from the said optical portion, said other loop appendage defining a curvilinear "C" shape, the outer distance of both loops from the optical portion along its central axis being equal.

10 Claims, 3 Drawing Sheets

ARTIFICIAL EYE LENS AND METHOD OF IMPLANTING SAME

FIELD OF THE INVENTION

The present invention relates to artificial lenses for eyes, in general, and to soft intraocular lenses and a method for implanting them in the posterior chamber, in particular.

BACKGROUND OF THE INVENTION

A number of eye diseases exist wherein it is necessary to surgically remove the natural lens of the eye. During such surgery, it is necessary to replace the lens with an artificial lens, if the patient is to regain the use of the eye. Numerous artificial lenses have been developed and disclosed in the patent literature. These include glass intraocular lenses or hard plastic lenses known as PMMA that are held in place in the eye with loops, clips, staves and sutures.

Lenses for insertion into the lens capsule are illustrated, for example, in U.S. Pat. Nos. 4,251,887, 4,254,510, 4,476,591 and 4,477,931. Lenses adapted for attachement to the ciliary body of the eye are disclosed, inter alia, in U.S. Pat. Nos. 4,253,199, 4,249,272 and 4,254,509. Still other artificial intraocular lenses are disclosed in U.S. Pat. Nos. 4,253,200, 4,254,511, 4,257,130, 4,480,340, 4,338,687 and 4,414,694. There is shown in U.S. Pat. No. 4,277,852 an intraocular lens with supporting mount which is automatically implantable with correct optical orientation of the correction axis.

These lenses are generally so-called hard lenses which are relatively inflexible. There are also known soft lenses made of a flexible material. Soft lenses require the selection of an appropriate material which is sufficiently flexible yet has the necessary optical qualities, which is non-toxic and which can be manipulated to the desired shape. They also require an effective design to provide a suitable optical region and effective fixation.

U.S. Pat. No. 4,424,597 to Schlegel discloses a posterior chamber implant lens comprising a homogeneous, clear, vulcanized silicone rubber optical portion and a radially outwardly extending, thin-walled support encircling the centerpoint of the lens body and having several openings distributed thereover. The lens of silicone rubber is flexible and of a constant size since it does not absorb fluid in the eye. Thus, in order to implant this lens, the incision must be as large as the lens, or the lens must be folded for insertion and then unfolded within the eye. Furthermore, this lens is very thin so that upon fibrosis, when the capsule constricts about it, the lens often pops out.

There is shown in U.S. Pat. No. 4,449,257 to Koeniger an intraocular soft lens of HEMA plastic cut into a round lens with concentric grooves around peripheral margins which frictionally engage the rough interior walls of the posterior lens capsule. Koeniger replaces the entire natural lens with an artificial lens of substantially identical shape and size. Due to the absorptive nature of the HEMA plastic material, when implanted, the dry lens softens by absorbing aqueous humour and expands to fill the lens bag. The disadvantages of this method are two fold. First, a relatively large incision is required through which the lens is inserted, due to the width of the lens. Second, since the power of the lens depends on its curvature, the lens of this shape detracts from normal vision because the size and shape of the lens physiologically does not permit the provisions of the necessary optical diopters, in the shape described.

There is shown in U.S. Pat. No. 4,253,199 a deformable implant lens including upper and lower pieces which are sealed around the edges thereof leaving a lip or flap on one or both pieces. The flap is attached to the ciliary body as by sutures. Insertion of the lens is accomplished while the implant lens is partially dehydrated. The point at which the lens pieces are bent to form the lip is a weak point about which the lens which can deform during dehydration, causing difficulty during insertion.

U.S. Pat. No. 4,573,998 broadly discloses numerous intraocular lens structures comprising a deformable optical zone portion and methods and instruments for implanting them.

U.S. Pat. No. 4,840,627 discloses artificial eye lenses and method for transplanting same wherein the lens comprises a hydrogel and defines symmetrically tapering fixation elements.

SUMMARY OF THE INVENTION

It is an object of the present invention to provide an intraocular PMMA lens including a central optical convex lens and two fixation support portions which permit easy and accurate implantation in the desired location in the eye.

There is thus provided in accordance with the present invention an intraocular lens comprising a central convex optical portion and two fixation loop appendages extending from the periphery of said optical portion substantially horizontally thereof, characterized in that one of said loop appendanges is double spring like and curves from said periphery of said optical portion in a curvilinear "reverse S" shape and the other said loop appendage extends from the same side of the periphery in the opposite direction in a curve from the optical portion and defines a curvilinear "C" shape, the outer distance of both loops from the optical portion being equal.

According to a preferred embodiment, the lens defined above further comprises an extension on the optical portion in the direction of the "C" shaped loop appendage, said extension having a hole for receiving a manipulating probe to facilitate adjustment of the lens in the eye during insertion thereof.

There is also provided in accordance with the present invention a method of operating in the eye including the steps of removing the lens of the eye and part of the anterior capsule portion, inserting said above lens into the bag of the lens, and positioning the lens implant into fixative contact in a predetermined location, i.e. in the equator of the bag.

BRIEF DESCRIPTION OF THE DRAWINGS

The lens of the present invention will be further understood and appreciated from the following detailed description taken in conjunction with the drawings in which.

DETAILED DESCRIPTION OF THE INVENTION

Figure 6:
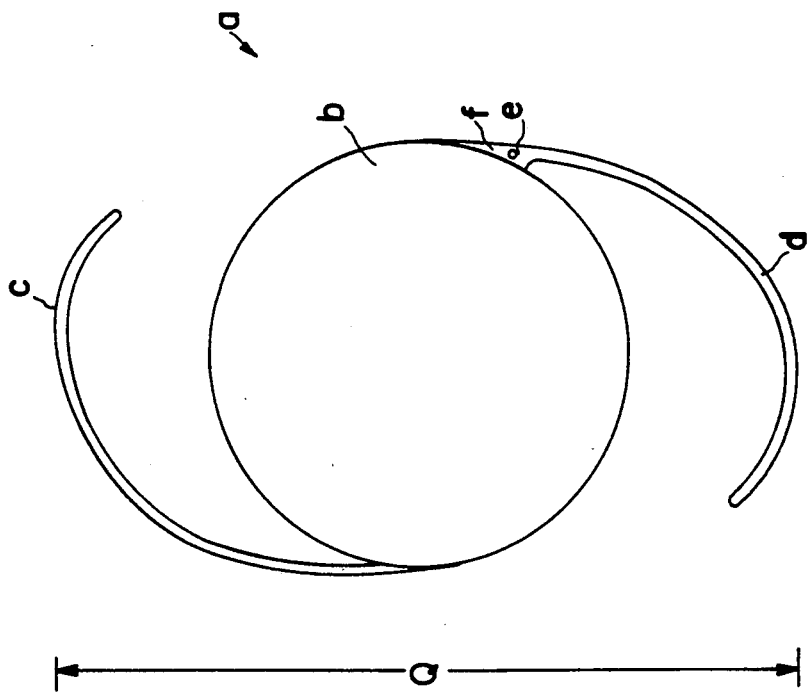
FIG. 6 illustrates a prior art intraocular lens with loop appendages.

Referring to FIG. 6, this illustrates an intraocular PMMA lens a of the prior art comprising an optical portion b and two substantially symmetrical fixation appendages c and d oppositely disposed. The overall length Q of lens a is generally 13.5–14.0 mm. Appendage d has a hole e at its base f where it meets the optical portion b. This hole e permits manipulation of the lens in the eye with a lens hook.

Figure 1:
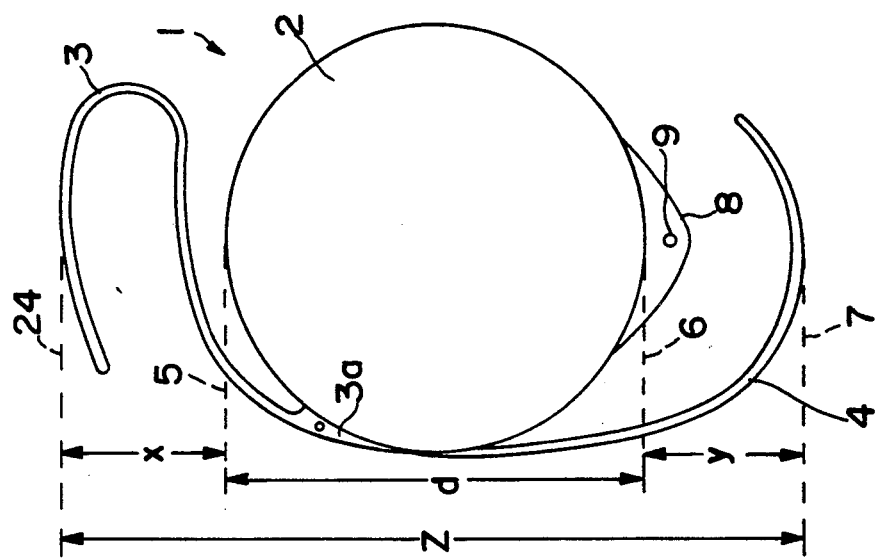
FIG. 1 is a plan view illustration of an intraocular lens constructed and operative in accordance with an embodiment of the present invention.
Figure 2:
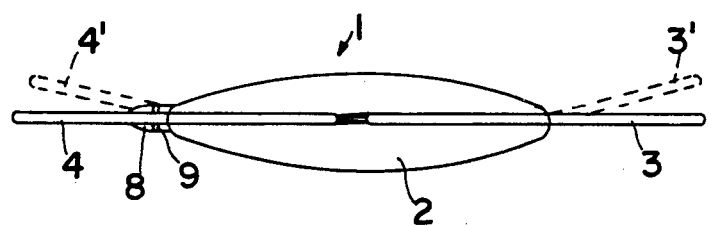
FIG. 2 is a side view of the lens of FIG. 1.

With reference to FIGS. 1 and 2 there is shown an intraocular lens 1 in accordance with the invention comprising optical portion 2 and two fixation loop appendages 3 and 4 which are not identical. Both loop appendages 3 and 4 extend from the same side of the optical portion 2 and curve therefrom substantially in the horizontal plane, as shown by 3 and 4, or slightly angled from zero to about 10 degrees as in 3' and 4', loop 3 curving in one direction in the general shape of a reverse letter "S" and loop 4 curving in the other direction in an approximate "C" shape. The distance X from the outer perimeter 24 of loop 3 to the upper periphery 5 of optical portion 2 is substantially the same as the distance Y from the outer perimeter 7 of loop 4 to the lower circumferential periphery 6 of optical portion 2. A horizontal arcuate extension 8 is provided at the lower periphery 6 of the optical portion 2 with a hole 9 therein for receiving a lens hook to facilitate manipulating of the lens during implantation. A similar manipulating hole 9a may optionally be provided at the base 3a of loop appendage 3. The overall length Z of the lens including the optical portion and fixation loop appendages is about 11 to 12 mm, and the diameter d of the optical portion 2 is about 6 to 7 mm. The loop appendages 3 and 4 have approximate thicknesses of 0.15 to 0.25 mm.

Figure 3:
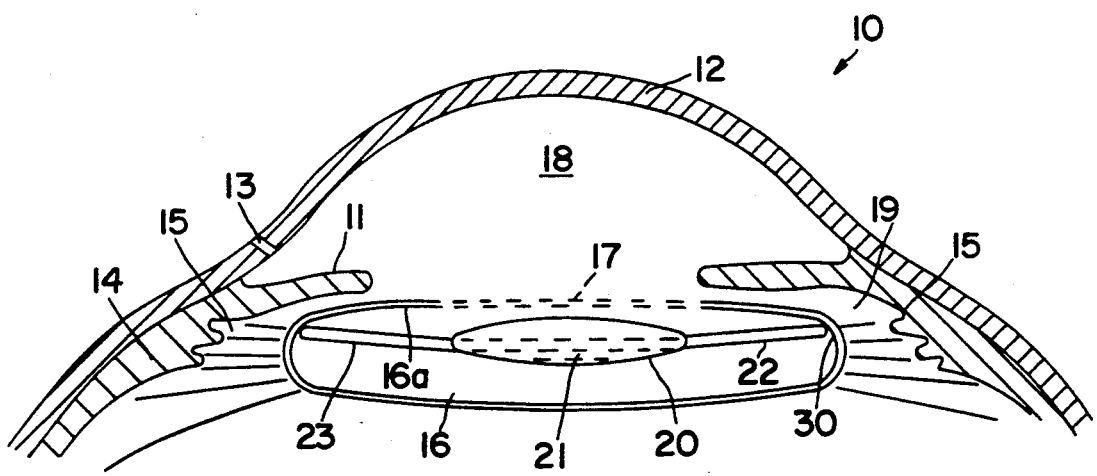
FIG. 3 is a schematic illustration of an eye with a lens inserted into the capsular bag in accordance with the present invention.

FIG. 3 illustrates schematically the lens of this invention held in the capsular bag after insertion. There is shown an eye 10 including a cornea 12, iris 11, limbus 13, ciliary body 14 and lens capsule 16. The ciliary body 14 defines the boundary between the so-called anterior chamber 18 and posterior chamber 19 with circular opening 17 made by round capsulorhexis capsulotomy. An artificial lens 20 according to the invention is placed in the capsular bag 16 with its optical portion 21 centered with respect to the circular opening 17 and its looped appendages 22 and 23 pressing against the equator of the bag 30.

Numerous procedures for the removal of cataracts have been developed. The most common one today is extra-capsular extraction, in which the round part of the anterior capsule is removed by means of capsulorhexis, i.e. tearing of the anterior capsule, leaving a round and continuous edge without outside extensions. This technique is called "round capsulotomy", wherein the round opening in the anterior capsule extends 4.0 to 7.0 mm in diameter, preferably about 5.5 mm.

Various types of capsulotomy, can-opener, or endocapsular, are being performed at present to achieve extra-capsular cataract extraction (ECCE). This type of capsulotomy, however, does not provide a closed capsular bag but rather an open bag so that when transplanting a lens therein the extended loops of the optical intraocular lens shown in FIG. 6 might extend out of the bag and come in contact with uveal tissue (pigment layer, ciliary process of ciliary muscle). The present invention involves round capsulorhexis capsulotomy leaving a closed collapsed bag with a diameter of 10.5 to 10.7 mm into which the novel lens can be introduced. According to the prior art, the overall diameter of the lens such as in FIG. 6 was about 13.5 to 14.0 mm. The lens of this invention, however, allows a better fit in the bag without extra spring tension of the loops 3 and 4 of FIG. 1 on the equatorial part of the bag. The new lens fits round capsulorhexis better than the lenses presently available, due to (a) its overall smaller diameter of 11.0 to 12.00 mm and (b) the special design of the loops 3 and 4 which are nonsymmetrical, one loop 3 being double curved spring-like and the other loop 4 having only a semi-circular spring loop.

Figure 4:
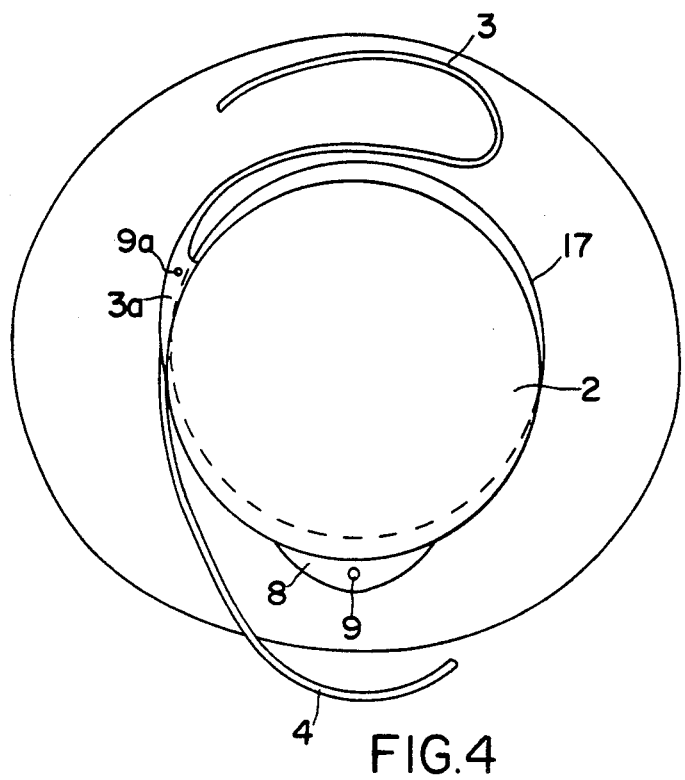
FIGS. 4 and 5 are schematic frontal and plan views respectively of the human eye having undergone capsularhexis with a lens according to the invention partially introduced therein.
Figure 5:
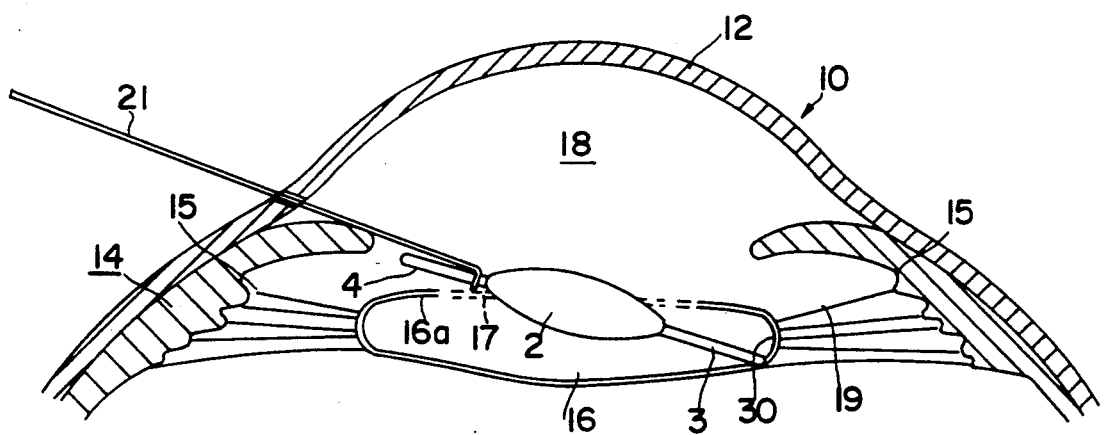

The method of introducing the lens into the capsulorhexis will now be discussed with reference to FIGS. 4 and 5. The double spring-like loop 3 is introduced into the opening 17 of the anterior capsule 16a by first pushing the lens 2 into the anterior chamber 18, then pushing it further through the small 5.5 mm round capsulotomy 17. The "reverse S" shaped loop 3 is so designed to facilitate its introduction into the bag 16 through this small circular opening 17 in the anterior capsule much more readily. The double spring-type design of loop 3 eases the manipulation of the lens by moving it as need be to the right and/or to the left or straight ahead during the forward pushing action without producing extra force on the capsulotomy edge. At this point the lens is half in the bag and half outside the bag, i.e. the "C" shaped loop 4 is still outside the bag (see FIG. 4) and does not have the tendency to be pushed out of the bag, due to its design. At this point, a lens hook of the Sinskey type 21 is attached to the hole 9 in the extension piece 8 and the hook 21 pushes the lens 2 further forward. The "C" shaped loop 4 then can slide into the bag 16 smoothly because of its semi-circular design pattern, and the pushing action on the lens enhances the sliding of the loop into the bag, which thus functions as a true closed bag without any tears in its opening perimeter. This overcomes the main disadvantage of the prior art lenses having symmetrical loops which require a relatively large capsulotomy or a radial tear in the perimeter of the bag. This prior art surgical procedure led to relatively high complication rates, such as posterior tear of the capsule, decentration of the lens, dislocation of the lens, permanent loop touch to uveal tissue with permanent low-grade uveitis. With the lens of the present invention, however, one can take advantage of round capsulorhexis making use of a relatively small 5.5 mm capsulotomy with no radial tear of the capsule towards the periphery of the bag.

It is course understood that the fixation loop appendages can be mirror images of those shown, i.e. one loop being "S" shaped and the other having a reverse "C" shape, and that the lens may be convex on both surfaces or only on one surface.

I claim:

1. An intraocular lens, insertable into the capsular bag after capsulorhexis capsulotomy, comprising a central convex optical portion with opposed lens surfaces and two fixation loop appendages having a base extending from the periphery of said optical portion and substantially in the horizontal plane thereof, characterized in that one of said loop appendages is double spring-like and curves from said periphery of said optical portion in a curvilinear "reverse S" shape, said loop being insertable first into said capsular bag, and the other said loop appendage extends from the same side of the periphery curving in the opposite direction in a curve from the said optical portion, said other loop appendage defining a curvilinear "C" shape which is smoothly slidable into said capsular bag, the overall length of the lens being between 11.0 and 12.0 mm, inclusive, and the outer distance of both loops from the optical portion along its central axis being equal.

2. A lens as in claim 1 which is made of PMMA.

3. A lens as in claim 1 wherein the optical portion is 6.0–7.0 mm.

4. A lens as in claim 1 comprising an extension of the optical portion at the base of the other, "C" shaped loop, said extension having a hole for insertion of a manipulating probe.

5. A lens as in claim 1 having a manipulating hole at the base of the "reverse S" shaped loop.

6. A lens as in claim 1 wherein the optical portion of the lens is convex on both lens surfaces.

7. A lens as in claims 1 wherein the optical portion of the lens is convex on only one lens surface.

8. A lens as in claim 1, wherein the optical portion is 6.5 mm.

9. A method of operating in the eye comprising the steps of:
removing the natural lens of the eye and part of the anterior capsule portion by a capsulorhexis capsulotomy, thus forming a bag;
inserting an intraocular lens as defined in claim 1 into said bag by first pushing the double spring-like "reverse S" shaped loop and part of the optical portion into said bag, and subsequently sliding the rest of the optical portion and said "C" shaped loop into said bag.

10. A method as claimed in claim 9 including the use of a lens hook for introducing the lens into the bag.

* * * * *